US006752776B2

(12) United States Patent
West

(10) Patent No.: US 6,752,776 B2
(45) Date of Patent: Jun. 22, 2004

(54) BODY SUPPORT HARNESS

(75) Inventor: R. Gary West, Birmingham, AL (US)

(73) Assignee: HealthSouth Corporation, Birmingham, AL (US)

( * ) Notice: Subject to any disclaimer, the term of this patent is extended or adjusted under 35 U.S.C. 154(b) by 303 days.

(21) Appl. No.: 10/082,153

(22) Filed: Feb. 26, 2002

(65) Prior Publication Data

US 2003/0162636 A1 Aug. 28, 2003

(51) Int. Cl.[7] ..................................................... A61F 5/00
(52) U.S. Cl. ............................................ 602/36; 602/32
(58) Field of Search ............................. 128/100.1, 99.1, 128/869; 601/23, 27, 33, 34, 35; 482/54, 69, 66, 51; 607/48, 49; 602/32, 36, 19, 23, 60, 61

(56) References Cited

U.S. PATENT DOCUMENTS

| | | | | | |
|---|---|---|---|---|---|
| 4,512,437 | A | * | 4/1985 | Savage | 182/3 |
| 5,502,851 | A | | 4/1996 | Costello | |
| 5,503,621 | A | * | 4/1996 | Miller | 602/19 |
| 5,660,445 | A | * | 8/1997 | Murray | 297/485 |
| 5,695,432 | A | * | 12/1997 | Soderlund | 482/69 |
| 5,765,738 | A | * | 6/1998 | Hoffner | 224/661 |
| 5,814,001 | A | * | 9/1998 | Schwenn et al. | 602/24 |
| 5,893,367 | A | * | 4/1999 | Dubats et al. | 128/875 |
| 6,578,594 | B1 | * | 6/2003 | Bowen et al. | 135/67 |
| 6,588,022 | B1 | * | 7/2003 | Anders et al. | 2/421 |
| 6,689,075 | B2 | * | 2/2004 | West | 601/23 |

* cited by examiner

*Primary Examiner*—Henry Bennett
*Assistant Examiner*—Camtu Nguyen
(74) *Attorney, Agent, or Firm*—Bradley, Arant, Rose & White

(57) ABSTRACT

A torso support portion and a pair of thigh support portions are each formed of an outer layer of hard relatively stiff molded plastic material of limited flexibility and an inner layer of relatively soft cushioning material for distributing the weight of a patient over a large area. Three tightening straps serve to tighten the torso support portion about a patient with the parts of the torso support portion adjacent the free sides thereof overlapping one another in operative position. A pair of tightening straps serve to tighten each of the thigh support portions about the thighs of a patient with the free sides of each thigh support portion spaced a substantial distance from one another in operative position. Four adjustable suspension straps are provided for suspending the torso support portion and provide a quick-release feature. Each of the thigh support portions is connected to the torso support portion in depending relationship therefrom by three adjustable connecting straps. One of the thigh support portions is provided with a channel extending from the top edge to the bottom edge thereof portion for receiving a catheter. The thigh support portions are provided with outwardly facing fastening portions for fastening the thigh support portions to a powered gait orthosis device.

11 Claims, 3 Drawing Sheets

BODY SUPPORT HARNESS

The present invention relates to a body support harness which is particularly adapted to support the weight of the body of a patient on a powered gait orthosis device such as that disclosed in copending U.S. patent application Ser. No. 09/938,825, the disclosure of which is incorporated herein by reference. Such devices aid in research and rehabilitation of non-ambulatory patients and provide therapeutic exercise for those with spinal cord injuries.

BACKGROUND OF THE INVENTION

The present invention is an improvement over the harness construction as shown in U.S. Pat. No. 5,502,851 which is specifically designed for supporting the weight of the body of a patient on a device used for rehabilitation and physical therapy purposes. This prior art harness is made from soft fabric material which causes serious problems in use. The fabric which forms the lumbar support belt and the thigh wraps of this prior art harness tends to bunch up when supporting the weight of a patient so that undesirable areas of high pressure are created in localized areas on the patients body. Accordingly, the patient's weight is not well distributed and there is a tendency for the harness material to pinch the skin of the patient. This is, of course, very undesirable.

Furthermore, the patented harness employs a pair of shoulder straps which tend to squeeze the shoulders of the patient when suspended in the harness.

SUMMARY OF THE INVENTION

A primary objective of the present invention is to overcome the disadvantages of the prior art discussed above and provide a harness which successfully distributes the weight of the patient over a wide area and prevents any bunching up of the weight supporting portions of the harness disposed adjacent the patient's body, and which eliminates pinching of the patient's skin. Additionally, the suspension strap means of the invention prevents any squeezing of a patient's shoulders when suspended within the harness.

The harness of the invention comprises a torso support portion and a pair of thigh support portions which are connected to the torso support portion and depend therefrom. Each of these support portions is formed of an outer layer of hard relatively stiff molded plastic material of limited flexibility and an inner layer of relatively soft cushioning material. This construction ensures that there will be no bunching up of these components when supporting a patient, thereby distributing the weight over a wide area and preventing pinching of the patient's skin. Although the outer layer is hard, the inner layer is sufficiently soft so that it can conform to the contours of a patient's body and will be comfortable in use.

The torso support portion of the invention has opposite free sides, and is so constructed and arranged that the parts of the torso support portion adjacent to the free sides thereof overlap one another in operative position on the torso of a patient. This ensures that the torso of the patient will not be pinched and the patient's weight is distributed over a maximum area of the torso support portion.

The thigh support portions of the invention also each have opposite free sides, but these support portions which have a lesser weight support function than the torso support portion are so constructed and arranged that the free sides thereof are spaced from one another a substantial distance to ensure that the thighs of a patient will not be pinched.

The suspension strap means of the present harness includes four spaced suspension straps which are connected to the torso support portion at widely spaced points. The suspension straps are disposed substantially vertically from the torso support portion and are spaced from the shoulders of a patient, thereby ensuring that there will be no squeezing of the shoulders when the harness is in operative position.

Since the thigh support portions include an outer layer formed of a hard relatively stiff molded plastic material of limited flexibility, a special provision must be made to accommodate a catheter which is often present when treating the type patients with spinal cord injuries and the like. Normally, the patient will wear some sort of pants, and if a catheter is present, it will be under the pants. Therefore, it is necessary to provide a channel extending from the top edge to the bottom edge of one of the thigh support portions for receiving the material of the pants and the catheter so that the catheter is not damaged during use of the harness. Such a channel is provided as an integral part of one of the thigh support portions of the harness Additionally, the thigh support portions are provided on the outer surface thereof with fastening portions for fastening the thigh support portions to a powered gait orthosis device.

DESCRIPTION OF THE PREFERRED EMBODIMENT

Figure 1:
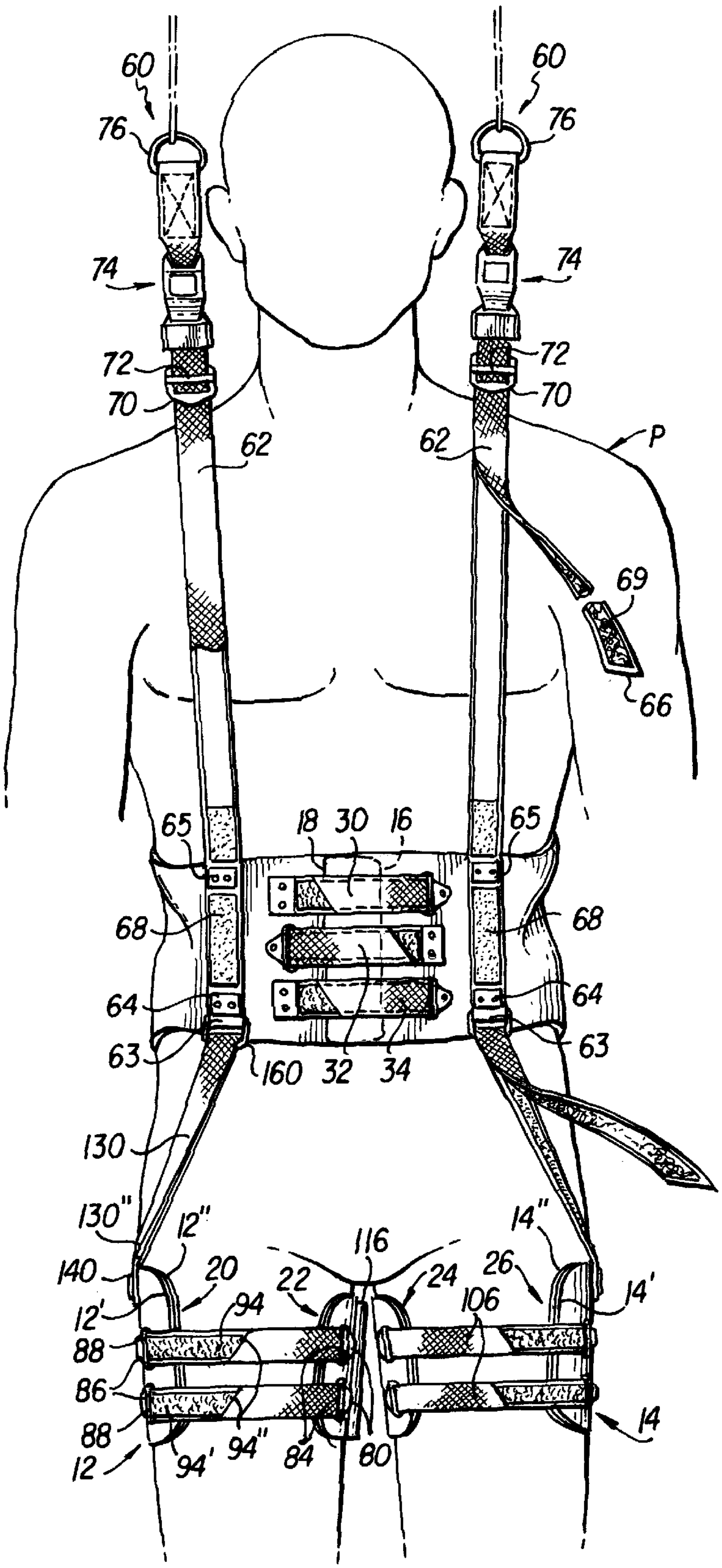
FIG. 1 is a front view of the invention harness mounted in operative position upon the body of a patient.

Referring now to the drawings wherein like reference characters designate corresponding parts throughout the several views, a patient P is shown with the invention harness mounted in operative position on his body. The harness includes a torso support portion 10 and a pair of thigh support portions 12 and 14. The torso support portion is formed of an outer layer 10' and an inner layer 10", the inner layer being vulcanized to the inner layer or otherwise affixed thereto. The outer layer is formed of a hard relatively stiff molded plastic material of limited flexibility such as PETROTHENE, a medium density polyethylene manufactured by Equistar Chemicals of Houston Tex. This plastic material has a density nominal value of 0.930 g/cc. The inner layer is formed of a relatively soft cushioning material such as pure gum sponge rubber in the form of elastic, open cell sheeting. The cushioning material has a density of 22 lbs/cu ft and has a Durometer hardness, Shore 00 of 30–50. The cushioning material also has compression (25% deflection) of 2–5 psi and tensile strength of 2–5 psi. The combination of these inner and outer layers enables the torso support portion to distribute the weight of the patient over a wide area while providing a comfortable fit for the patient.

The pair of thigh support portions 12 and 14 are also formed of outer layers 12' and 14' respectively and inner layers 12" and 14" respectively. These outer and inner layers are secured to one another in the same manner as in the torso support portion. The outer and inner layers of the thigh support portions are formed of the same material as the outer and inner layers respectively of the torso support portion.

The torso support portion has opposite free sides 16 and 18. Thigh support portion 12 has opposite free sides 20 and 22, and thigh support portion 14 has opposite free sides 24 and 26. As seen in FIG. 1, when the torso support portion is mounted on the patient in operative position, the parts of the torso support portion adjacent to the free sides 16 and 18 thereof overlap one another. When the thigh support portions 12 and 14 are mounted on the patient in operative position, the free sides thereof are spaced a substantial distance from one another. With this arrangement, pinching of the patient's skin is avoided.

Figure 3:
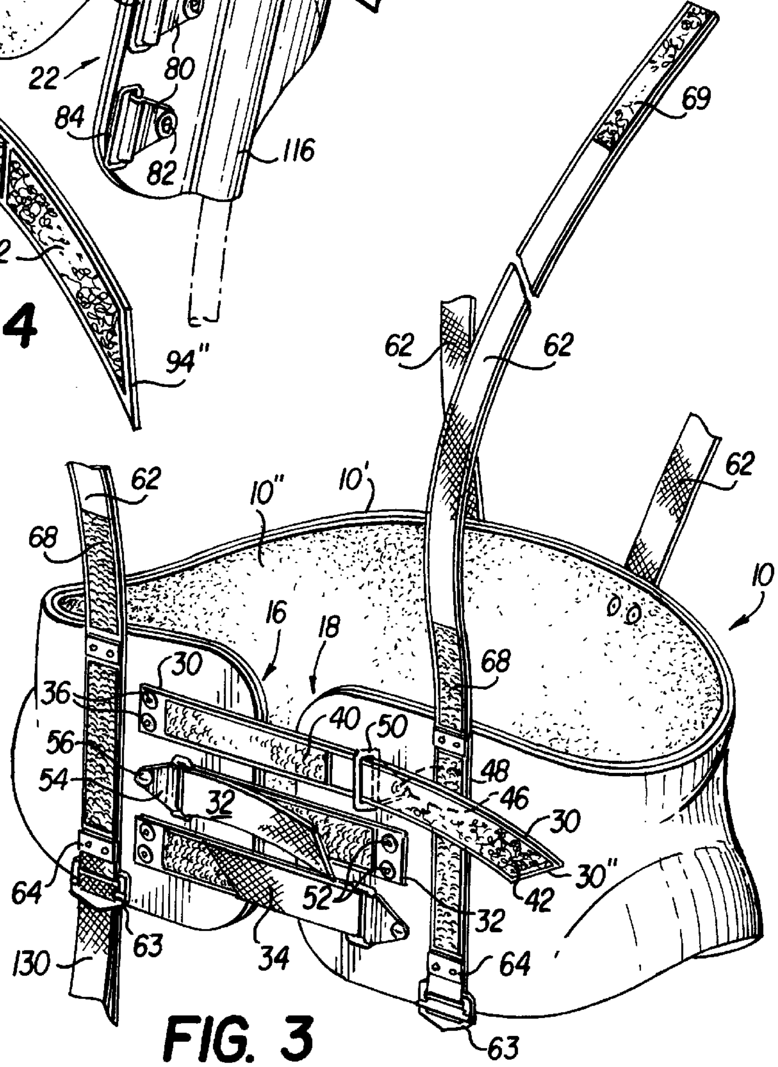
FIG. 3 is a top perspective view of the torso support portion of the harness prior to mounting on a patient.

Three tightening straps 30, 32 and 34 are provided for tightening the torso support portion about a patient and for securing the parts of the torso support portion adjacent to the free sides thereof in overlapping relationship to one another. As seen in FIG. 3, strap 30 has one end 30' thereof fixed to the torso support portion near the free side 16 thereof by nut and bolt assemblies 36. Each of assemblies 36 includes a bolt extending inwardly through aligned holes in the strap and the torso support portion. The inner end of the bolt is threaded into a threaded stem of a nut having a disc-like head which engages the inner face of the inner layer of the torso support portion. Such nut and bolt assemblies are of conventional construction and are referred to as a Chicago screw or binding screw assembly. Similar nut and bolt assemblies are utilized throughout the harness construction. In the case of assemblies, 36, the bolt extends through a washer which engages the outer face of strap 30.

The other end 30" of strap 30 is free. The outer face of strap 30 has a first portion 40 and a second portion 42 of a hook and loop fastener supported thereon at an intermediate For example, portion 40 may comprise the hook portion and portion 42 may comprise the loop portion. These hook and loop portions are disposed at a portion of the strap which is intermediate the opposite ends thereof. A plastic fitting 46 is fixed to the torso support portion near the free side 18 of the torso support portion by a nut and bolt assembly 48; and fitting 46 pivotally supports a metal loop 50. The intermediate portion of strap 30 passes through loop 50. It is apparent that when it is desired to tighten and secure the torso support portion in position, the free end of strap 30 is passed through loop 50 and then pulled as hard as desired. The strap is then doubled back on itself to engage fastener portions 40 and 42 with one another to secure the torso support in adjusted position.

Strap 32 is of similar construction to strap 30 except that the position thereof is reversed. The end 32' of strap 30 is fixed to the torso support portion near the free side 18 thereof by nut and bolt assemblies 52, and a fitting 54 is fixed to the torso support portion near the free side 16 thereof by a nut and bolt assembly 56. The outer face of strap 32 is provided with hook and loop connector portions in the same manner as strap 30 and operates in the same manner as strap 30. Strap 32 enables a therapist to effectively tighten strap 32 in the opposite direction from which strap 30 is effectively tightened, so that the torso support portion can be adjusted from opposite sides of the patient. Strap 34 is of the same construction as strap 30 and operates in the same manner, and accordingly, no further discussion of strap 34 is necessary. It is noted that strap 34 is shown in the secured position in FIG. 3, while all three straps are shown in secured position in FIG. 1.

Four suspension strap means 60 are provided, these straps being identical in construction, and accordingly, similar reference numerals are applied to each of the straps means. Each suspension strap means includes a lower strap 62 having a lower end 63 fixed to the torso support portion by a pair of spaced metal plates 64 and 65 which are fixed to the torso support portion by nut and bolt assemblies as previously described. The opposite end 66 of each lower strap is free, and each lower strap includes an intermediate portion between the opposite ends thereof. Each lower strap includes separate hook and loop fastener portions 68 and 69 on the outer face of the strap adjacent the opposite ends thereof. For example, 68 may be the hook fastener portions and 69 may be the loop fastener portions.

Each suspension strap means also includes a metal loop 70 having a sliding metal bar 72 of conventional construction. The intermediate portion of the lower strap extends through loop and is wrapped around the bar so that the bottom strap is doubled back on itself and the hook and loop portions are engaged with one another to hold the suspension strap means in adjusted position. It is apparent that the length of the lower strap between loop 70 and the torso support portion can be adjusted by unloading the lower strap and moving it through loop 70 until the desired position is reached whereupon the lower strap can be loaded to hold it in position.

Each suspension strap means also includes a quick-release buckle 74 as used in the seat belts on airplanes, this buckle having a first side which is pivotally connected to loop 70 and an opposite side which is connected to a connector member 76 such as a metal D-ring which is adapted to connect the harness to a powered gait orthosis device.

Figure 4:
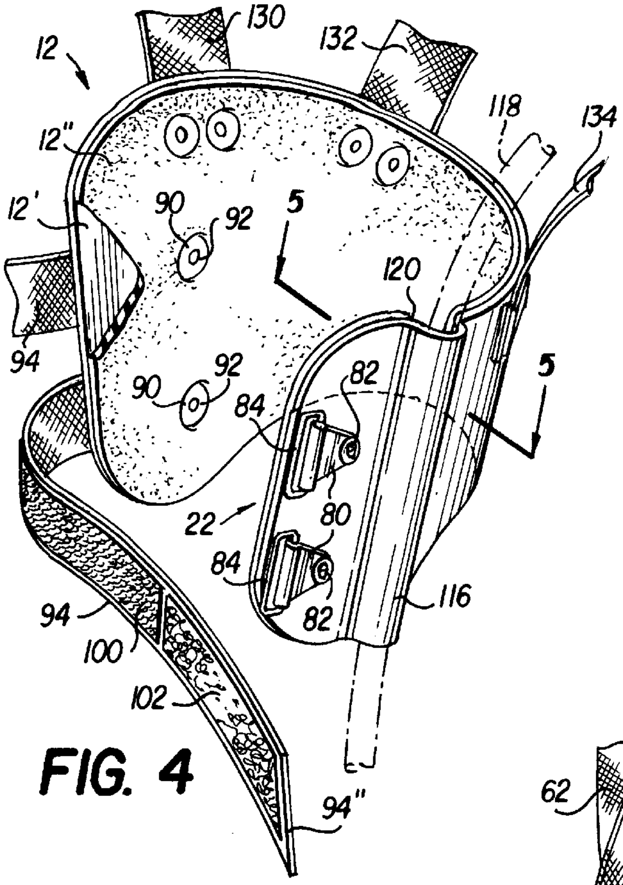
FIG. 4 is a top perspective view of the thigh support portion of the harness prior to mounting on a patient.
Figure 5:
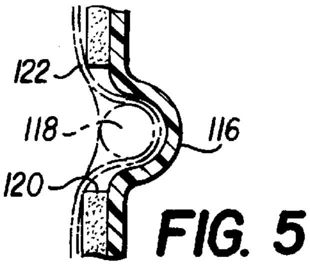
FIG. 5 is a cross-section through the thigh support portion taken along line 5—5 of FIG. 4.

The construction of thigh support portion 12 is seen in FIGS. 4 and 5 wherein it is seen in its normal relaxed position. The interior of portion 12 generally defines a frusto-conical configuration, or in other words it tapers downwardly and inwardly so that it will not tend to ride up on a patient's thigh when in use. A pair of similar plastic fittings 80 are fixed to portion 12 adjacent free side 22 thereof by nut and bolt assemblies 82 similar to those previously described. A metal loop 84 is pivotally supported by each of fittings 80. A similar pair of plastic fittings 86 as seen in FIG. 1 are similarly fixed to portion 12 adjacent free side 20 thereof, and each of such fittings pivotally supports a metal loop 88 similar to loops 84. The disc-like heads 90 of the nuts and the ends of the bolts 92 threaded thereinto of the nut and bolt assemblies fixing plastic fittings 86 to portion 12 are visible in in FIG. 4.

A pair of tightening straps 94 are provided and each has one end 94' passing through an associated loop 88 and doubled back on itself and stitched in place to pivotally connect end 94' to the loop. The opposite end 94" of each strap 94 is free. An intermediate portion of each strap 94 is provided between the opposite ends thereof, and separate hook and loop fastening portions are disposed on one face thereof. A first fastening portion 100 may be a hook portion and a second fastening portion 102 may be a loop fastening portion.

When it is desired to tighten and secure thigh support portion 12 in place, the free ends of straps 94 are passed through loops 84 and doubled back on straps 94 so that the fastening portions thereof are in engagement with one another to secure the thigh support portion in operative position.

Thigh support portion 14 is of similar construction to thigh support portion 12 and is basically a mirror image thereof. A pair of tightening straps 106 are similar to straps 94 of thigh support portion 12 and are mounted and operate in the same manner as straps 94 except in the opposite direction. Therefore, no further description of the details of thigh support portion 14 is necessary.

Figure 2:
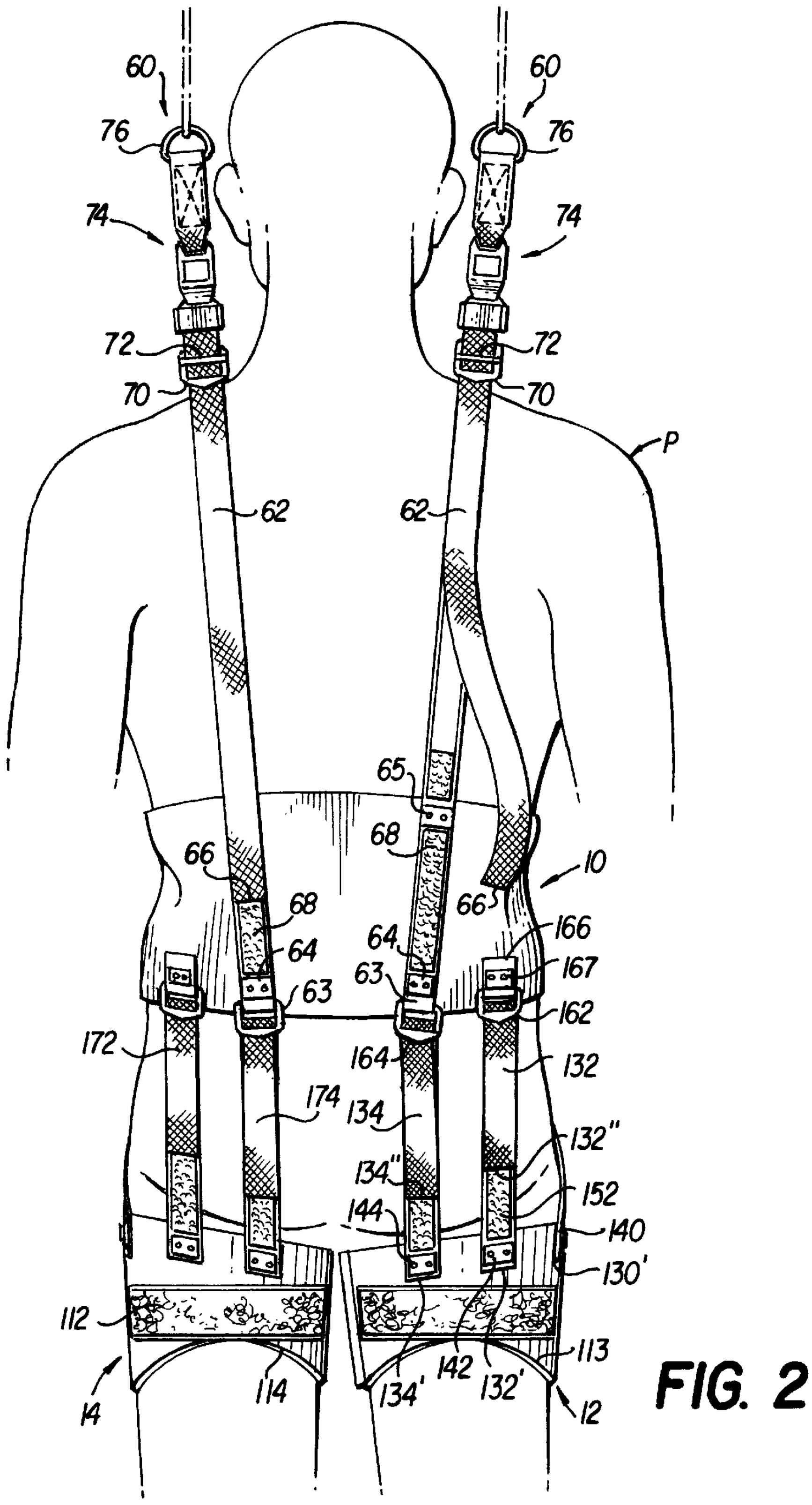
FIG. 2 is a rear view of the invention harness mounted in operative position upon the body of a patient.

As seen in FIG. 2, the rear side of thigh support portions 12 and 14 are provided with an outwardly facing hook and loop fastening portions 110 and 112 respectively. These fastening portions may be secured to the outer layer of the thigh support portions by suitable adhesive means. Each of fastening portions 110 and 112 may for example comprise loop portions which are adapted to engage hook portions on parts of a powered gait orthosis device so that motions of the orthosis device may be transmitted to the thigh support portions and thence to the thighs of the legs of a patient using the orthosis device. Thigh support portions 12 and 14 also have arcuate cutouts 113 and 114 respectively in the bottom edges of the rear sides thereof.

As seen in FIGS. 4 and 5, thigh support portion 12 differs from thigh support portion 14 in that the outer layer 12' includes an outwardly extending integral molded part 116 which is of generally semi-circular cross-section extending from the top edge to the bottom edge of thigh support portion 12 and which defines a channel for receiving a catheter 118 shown in phantom line in FIG. 5. A cutout 120 is formed in the inner layer 12" and also extends from the top edge to the bottom of thigh support portion 12 for receiving part of the catheter. A piece of fabric 122 is illustrated in FIG. 5 to show the manner in which the fabric of a pant leg as well as a catheter carried by a patient fits within the channel and cutout thereby preventing any damage to the catheter when the thigh support is tightened and secured around a patient's leg. It should be understood that there is no corresponding part 116 or cutout 118 in thigh support portion 14, and the inner and outer layers of thigh support 14 are continuous curves from one free side to the other free side thereof.

Thigh support portion 12 is connected to the torso support portion in depending relationship therefrom by three connecting straps 130, 132 and 134 the lower ends 130', 132' and 134' of which respectively are fixed to thigh support portion 12 by three plates 140, 142 and 144 and nut and bolt assemblies as previously described. The straps have opposite ends 130", 132" and 134" which are free. Each of the connecting straps has separate hook and loop fastening portions on one face thereof at an intermediate portion between the opposite ends thereof. The fastening portions 152 and 154 adjacent the lower ends of connecting straps 132 and 134 can be seen in FIG. 2. A similar fastening portion (not shown) is provided on strap 130.

The fastening portions adjacent the free ends of straps 130, 132 and 134 are not visible in the drawings, but it will be understood that they are in facing contact with the previously mentioned fastening portions adjacent the lower ends of the straps when the connecting straps are doubled back on themselves as shown in FIGS. 1. and 2.

The intermediate portions between opposite ends of connecting straps 130, 132 and 134 pass through loops 160, 162 and 164 respectively, each of these loops having a sliding bar with the associated connecting strap wound therearound with each connecting strap being doubled back on itself and with the separate fastening portions thereon in contact with one another. This enables the position of thigh support portion 12 to be adjusted relative to the torso support portion in a well-known manner.

Loop 160 is pivotally supported by the lower end 63 of one of the suspension straps 62 as seen in FIG. 1. Loop 162 is pivotally supported by a short strap 166 fixed to the torso support portion by a plate 167 and nut and bolt assemblies as previously described. Loop 164 is pivotally supported by the lower end 63 of one of the suspension straps as seen in FIG. 2.

Thigh support portion 14 is connected to the torso support portion in depending relationship therefrom by three connecting straps 170, 172 and 174 which correspond to straps 130, 132 and 134 respectively of thigh support portion 12. Straps 170, 172 and 174 are of the same construction and operate in the same manner as straps 130, 132 and 134 discussed in connection with thigh support portion 12. Therefore, no further explanation is required regarding the construction of connecting straps 170, 172 and 174 and the manner in which they adjustably connect thigh support portion 14 to the torso support portion.

The invention has been described with reference to a preferred embodiment. Obviously, various modifications, alternatives and other embodiments will occur to others upon reading and understanding this specification. It is my intention to include all such modifications, alternatives and other embodiments insofar as they come within the scope of the appended claims or equivalents thereof.

What is claimed is:

1. A body support harness for supporting a patient comprising, a torso support portion for fitting around the torso of a patient, a pair of thigh support portions connected to said torso portion and depending therefrom, a plurality of suspension strap means for suspending said torso support portion, said torso support portion and said thigh support portions each having opposite free sides and each being formed of an outer layer of hard relatively stiff molded plastic material of limited flexibility and an inner layer of relatively soft cushioning material for distributing the weight of a patient over a large area, and securing means for tightening and securing said torso support portion and each of said thigh support portions about parts of a patient's body.

2. A harness as defined in claim 1 wherein the free sides of each of said thigh support portions are spaced a substantial distance from one another when in operative position on the thighs of a patient.

3. A harness as defined in claim 1 wherein the parts of the torso support portion adjacent to said free sides of said torso support portion overlap one another when in operative position on the torso of a patient.

4. A harness as defined in claim 1 wherein said suspension strap means are four in number, each of said suspension strap means including a lower strap having a lower end, an intermediate portion and an opposite end, said lower end being fixed to said torso support portion, said opposite end being free, said lower strap having separate hook and loop fastening portions on one face of said intermediate portion, a loop including a sliding bar, said intermediate portion extending through said loop and being wrapped around said bar, a quick-release buckle having opposite buckle sides, one of said buckle sides being connected to said loop, and a connector member being connected to the other of said buckle sides.

5. A harness as defined in claim 1 including a plurality of tightening straps for tightening said torso support portion and securing the parts of the torso support portion adjacent to said free sides thereof in overlapping relationship to one another, each of said tightening straps having opposite ends and including an intermediate portion, one of said ends being fixed to said torso support portion near one of the free sides thereof, the other end of each of said tightening straps being free, a plurality of loops, each of said loops being pivotally supported by said torso support portion for receiving one of said tightening straps, each of said loops being disposed near the free side of the torso support portion opposite to the free side near which the fixed end of the associated tightening strap is disposed, each of said tightening straps having separate hook and loop fastening portions on one face thereof at said intermediate strap portion, each of said intermediate portions passing through one of said pivotally mounted loops.

6. A harness as defined in claim 5 wherein said tightening straps include at least one strap which is fixed to said torso support portion near one of the free sides thereof and another strap which is fixed to said torso support portion near the other of the free sides thereof.

7. A harness as defined in claim 1 including a pair of tightening straps for tightening each of said thigh support portions and securing the parts of each of the thigh support portions with the free sides thereof in spaced relationship to one another, each of said tightening straps of each of said thigh support portions having opposite ends and an intermediate portion, one of said ends being pivotally fixed to the associated thigh support portion near one of the free sides thereof, the other of said ends being free, a pair of loops, each of said loops being pivotally supported by the associated thigh support portion near the opposite free side thereof, each of said tightening straps having separate hook and loop fastening portions on one face of said intermediate portion, each of said intermediate portions passing through one of said pivotally mounted loops.

8. A harness as defined in claim 1 wherein each of said thigh support portions has three connecting straps for connecting a thigh support portion to said torso support portion, each of said connecting straps having a lower end, an intermediate portion and an opposite end, said lower end being fixed to an associated thigh support portion, said opposite end being free, each of said connecting straps having separate hook and loop fastening portions on one face thereof at said intermediate portion, said torso portion having a plurality of loops pivotally supported on the lower part thereof, the intermediate portion of each of said straps passing through one of said loops.

9. A harness as defined in claim 1 wherein one of said thigh support portions has top and bottom edges and includes an outwardly extending part which defines a channel extending from said top edge to said bottom edge for receiving a catheter.

10. A harness as defined in claim 9 wherein said channel is defined by an integral molded portion of generally semicircular cross-section in said outer layer, and an adjacent cut-out being formed in said inner layer.

11. A harness as defined in claim 1 wherein each of said thigh support portions includes an outwardly facing hook and loop fastening portion secured to the outer layer thereof for fastening the thigh support portions to a powered gait orthosis device.

* * * * *